US005490519A

United States Patent [19]
Hessel

[11] Patent Number: 5,490,519
[45] Date of Patent: Feb. 13, 1996

[54] TUBULAR PROTECTIVE DEVICE FOR PROTECTION AGAINST TRANSFER OF INFECTIOUS MATTER DURING SEXUAL INTERCOURSE

[75] Inventor: Lasse Hessel, Reading, England

[73] Assignee: Chartex International plc, London, United Kingdom

[21] Appl. No.: 341,138

[22] Filed: Nov. 16, 1994

Related U.S. Application Data

[63] Continuation of Ser. No. 210,076, Feb. 24, 1994, abandoned, which is a continuation of Ser. No. 27,842, Mar. 8, 1993, abandoned, which is a continuation of Ser. No. 727,637, Jul. 10, 1991, abandoned, which is a continuation-in-part of Ser. No. 621,850, Dec. 4, 1990, Pat. No. 5,094,250, which is a continuation of Ser. No. 148,992, Jan. 27, 1988, Pat. No. 4,976,273, which is a continuation of Ser. No. 58,766, Jun. 5, 1987, Pat. No. 4,735,621.

[51] Int. Cl.⁶ ................... A61F 6/02; A61F 6/04
[52] U.S. Cl. .................... 128/842; 128/844; 128/918
[58] Field of Search ................ 128/842, 844, 128/918; 604/330, 347–353

[56] References Cited

U.S. PATENT DOCUMENTS

| | | | |
|---|---|---|---|
| 32,566 | 4/1900 | Gagnier | 128/834 |
| 2,586,674 | 2/1952 | Lonne | 128/844 |
| 3,037,508 | 6/1962 | Friedman | 128/844 |
| 3,128,762 | 4/1964 | Young | 128/844 |
| 3,130,721 | 4/1964 | Young | 128/844 |
| 3,536,066 | 10/1970 | Ludwig | 128/842 |
| 4,832,052 | 5/1989 | Mohajer | 128/834 |

FOREIGN PATENT DOCUMENTS

| | | | |
|---|---|---|---|
| 0593216 | 2/1934 | Germany | 128/834 |
| 2703 | 9/1924 | Japan . | |
| 6311 | 5/1934 | Japan . | |
| 358535 | 4/1947 | Japan . | |
| 4688 | 6/1952 | Japan . | |
| 47-11199 | 2/1971 | Japan . | |
| 47-9299 | 2/1971 | Japan . | |

*Primary Examiner*—Michael A. Brown
*Attorney, Agent, or Firm*—Levy, Zito & Grandinetti

[57] ABSTRACT

The invention is a tubular protective device for protection against transfer of infectious matter during sexual intercourse and for use as a contraceptive. The tubular protective device includes a flexible, thin walled tube having a sufficiently large diameter to permit movement of a penis within the tube during coitus. The flexible thin walled tube also has a closed end and an open end. The open end has a ring-like member integrally connected to the open end. The protective device furthers includes a device for retaining the closed end of the tubular device in a vagina for a user.

2 Claims, 4 Drawing Sheets

TUBULAR PROTECTIVE DEVICE FOR PROTECTION AGAINST TRANSFER OF INFECTIOUS MATTER DURING SEXUAL INTERCOURSE

This application is a continuation of 08/210,076, filed Feb. 24, 1994, now abandoned, which is a continuation of 08/027,842, filed Mar. 8, 1993, now abandoned, which is a continuation of 07/727,637, filed Jul. 10, 1991, now abandoned, which is a continuation in part of 07/621,850, filed Dec. 4, 1990, now U.S. Pat. No. 5,094,250, which is a continuation of 07/148,992, filed Jan. 27, 1988, now U.S. Pat. No. 4,976,273, which is a continuation of 07/058,766, filed Jun. 5, 1987, now U.S. Pat. No. 4,735,621.

BACKGROUND OF THE INVENTION

1. Field of the Invention

This invention relates to a tubular protective device or condom-like device for protection against the transfer of infectious matter during sexual intercourse. Specifically, the invention relates to a thin-walled tubular protective device having a closed end and an open end wherein there is a means for retaining the closed end in a user.

2. Description of the Background Art

Condoms are devices that are used for both contraception and protection during sexual intercourse against the transfer of infectious matter such as bacterial and viral microbes that cause venereal diseases. The increase in the incidences of AIDS has caused various health organizations to encourage people to increase the use of condoms during sexual intercourse in order to prevent the spread of this fatal disease.

Condoms comprise a thin tubular casing, that is typically manufactured from latex and that has an open end and a closed end. Traditional condoms are drawn over the penis before coitus. The casing of a condom has an inner diameter that is selected so that the condom fits tightly on the penis. At the open end of a condom an elastic, flexible ring or rolled portion of latex is usually provided. This ring portion is the same diameter as the tubular casing of the condom. This elastic ring portion serves primarily to secure the condom on the penis and to prevent leakage of semen from the interior of the condom. Such elastic ring portions secure the open end of a condom onto the penis and do not radially extend the open end of the condom.

It is generally accepted that the AIDS virus can only be transferred through contact with the carrier's blood or blood plasma. During sexual intercourse such a transfer of the AIDS virus occurs when lesions of the carrier contact the mucous membrane or skin of the carrier's partner. Such a transfer of the AIDS virus is especially likely to occur at the base of the penis and at the vulva. There is a risk that lesions in these areas can be caused to bleed during sexual intercourse. When using a standard condom, these areas are unprotected or unshielded by the condom, and consequently a condom does not offer full protection against the transfer of infectious matter such as the AIDS virus.

Numerous attempts have been made to design a condom or condom-like device that provides effective contraception and/or more protection against the transfer of infectious matter than the standard condom. A sampling of these attempts are described below.

An article, "Outline For Successful Prophylactic Program" (Waterbury, Conn.: The Hemingway Press, 1934), the Gee Bee Company, 7–16, discloses a prophylactic device entitled, "The Gee Bee." This device is a loose fitting tubular prophylactic having a grooved outer ring. The grooved outer ring does not form a collar-shaped, outwardly extending portion at the open of the prophylactic. This invention does not disclose any description of a "female" embodiment having a means for retaining the closed end of the device in the vagina.

German Patent Number 210,413 to Hollmann discloses a condom-like device having an outer ring. The outer ring of this invention radially extends the opening of the condom. This invention has no means for retaining the closed end of the device in the vagina.

U.S. Pat. No. 899,251 to Graham discloses an animal breeder's bag. The bag is a condom-like device for livestock that can be used to collect semen. The bag contains a fixed inner band that is positioned at about the middle of the device. This position for the attachment of the band provides for a tube and a bag-like extension. The purpose of the band and cross strips is to collect semen in a pocket. A rubber frame can be made in various shapes, but is not disclosed as forming a collar-shaped, outwardly extending portion at the opening off the prophylactic. The band of this device is designed and positioned on the device in order to provide a semen collection bag. The band does not have a structure that is located at the closed end of the device to provide a retaining means such as is required for a "female condom".

U.S. Pat. No. 4,004,591 to Freimark discloses a birth control device. This birth control device is a female condom made of a strong rubber, plastic, or other similar material. This condom has a rigid, ring-like rim that is bent or scalloped. This rim can be a wire. The rim is not adapted to radially extend the open end of this device because this device is a hard molded material and not flexible. The cross-sectional dimensions of this condom are disclosed as being sufficiently large to easily accommodate the average width of the penis with some additional clearance space. The primary function of this device is to prevent unwanted pregnancy. This device is useful in preventing the spread of venereal disease. This device provides no means at the vulva to prevent an exchange between partners of secreted fluids that can contain venereal disease. Additionally, this birth control device is intended for use by females, but includes no means to secure or maintain the device in the vagina.

U.S. Pat. No. 4,630,602 to Strickman et al. discloses a disposable contraceptive cervical barrier. The cervical barrier of this invention is similar to standard diaphragms in size and design. This cervical barrier contains various "cavities for cells" that can hold spermicidal lubricants. These spermicidal lubricants can also be placed in numerous grooves within the body of the cervical barrier. Urethane polymers are used to make the device. The cervical barrier of this invention, unlike a condom, has no tubular side walls to prevent the exchange of secretion between partners that can contain a venereal disease.

The industry is lacking a simple, easy-to-use device that provides protection against the transfer of body fluids between partners during sexual intercourse and that can be securely retained in the vagina for a prolonged period of time before coitus.

SUMMARY OF THE INVENTION

The invention is a tubular protective device for protection against a transfer of infectious matter during sexual intercourse. The tubular protective device comprises a flexible, thin walled tube desirably having a sufficiently large diameter to permit movement of a penis within the tube during coitus. The flexible thin walled tube also has a closed end and an open end. The open end has a ring-like member integrally connected to the open end. The tubular protective device further comprises a means for retaining in a vagina at the closed end of the tubular protective device.

A desirable embodiment of the invention is a female condom like device or vaginal shield. This embodiment is a tubular protective device that comprises a flexible, thin-walled tube having a closed end and an open end. This embodiment also has a outwardly extending ring-shaped means that radially extends the open end and a retaining means at the closed end. The retaining means is molded into or extruded onto the closed end of the tubular protective device. The retaining means secures or maintains the tubular protective device in the vagina.

DESCRIPTION OF THE PREFERRED EMBODIMENT

Figure 1:
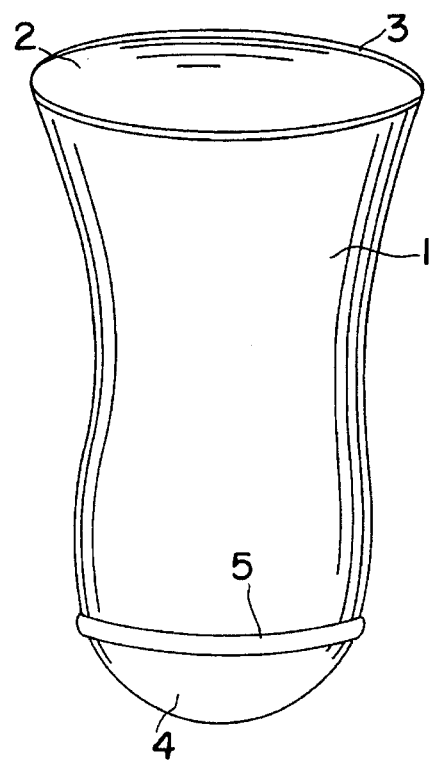
FIG. 1 is a perspective view of the protective device of the preferred embodiment of this invention.

The invention is based on the discovery that a particularly good protection against the transfer of infectious matter, including the AIDS virus, is obtained when a condom-like or tubular protective device is used during sexual intercourse. This protection is enhanced if the tubular protective device has at its open end an outwardly extending collar that is connected to a rigid ring-like means. The ring-like means is, desirably, adapted to maintain the collar of the device in a radially extended or stretched condition. The collar is preferably of a dimension that covers the vulva completely. The tubular protective device desirably has a sufficiently large inner diameter to allow movement of a penis with respect to the walls of the tubular device. The walls of the tubular device are held in a relatively immovable state or condition within and against the vaginal wall by a "means for retaining" or, simply, a retaining means. The means for retaining is desirably a ring-like member which is either removable or integrally connected to the closed end of the tubular protective device. The means for retaining can also be a band-like structure, longitudinal segments, or a cap-like structure. The collar covering the vulva is, also, essentially immovable with respect to the vulva during coitus.

The flexible, thin-walled tube of the invention is desirably cylindrical in shape and has an open end and a closed end. The tube is preferably made from a natural or synthetic polymer material. Desirable polymer materials are members selected from the group consisting of a latex, a polyethylene, a polyurethane, and derivatives based upon these polymers. The preferred material is a polyether polyurethane that has a soft, nonadhesive "hand feel". Other polymers or plastics such as polyolefins can be used to manufacture the tube of this device.

The tube of this device can be manufactured by numerous methods that are standard within the industry for fabricating items from polymer materials. The particular method chosen to manufacture the device of this invention varies with the particular polymer material chosen. An acceptable method of manufacturing the device can include curing a polymer material, such as latex, on a mold that has been dipped into a container of heated, liquified polymer material. Other methods can include either vacuum forming or blow molding a sheet of hearted polymer material into or onto a mold. Vacuum forming and blow molding are desirable with synthetic polymer materials such as polyurethanes.

The preferred method for manufacturing the device, when it is made of a synthetic polymer such as polyurethane, is to heat seal two layered sheets of the polymer material together to form the desired shape of the device. Heat sealing methods can be undesirable if caution is not exercised during the process. This is because these methods can leave hardened seams that can potentially irritate skin and mucous membrane surfaces. Additionally, the seams are subject to leakage and tearing if the heat sealing method is performed at an undesirably high temperature. Heat sealing methods, however, are desirable because the sheets of polymer material are not stretched during the manufacturing of the device and a consistent wall thickness for the device can be obtained.

The wall thickness of the tubular protective device can vary greatly. Typically, thinner wall thicknesses for the device allow more sensitivity during coitus. Wall thicknesses can be varied depending upon the strength of the polymer material that is chosen for the device. Preferably, a wall thickness for the device is between 20 and 60 microns ($\mu$m) for synthetic materials such as polyurethanes and 30 to 90 microns for natural materials such as latex. A wall thickness, regardless of the material from which the device is manufactured, must provide a tensile strength of at least 17 MPa when tested less than 12 months after manufacture and at least 15 MPa when tested 12 months or more after manufacture in order to comply with the standards of the American Society for Testing and Materials.

The internal or inner diameter of the tubular protective device in its unstretched state is desirably of a sufficiently large dimension to permit movement of a penis with respect to the protective device during sexual intercourse. The invention can have an inner diameter that causes the tubular protective device to be form fitting, but form fitting condom devices do not permit adequate sensitivity for the male during sexual intercourse. This is because a form fitting condom moves with the penis and prevents direct contact between the vaginal wall and the glans area during intercourse. This undesirable effect of form fitting condoms discourages their use by many members of the public. A tubular protective device having a large inner diameter merely functions as a liner for the vaginal wall or "vaginal pouch". In this situation the device is relatively stationary to the vaginal wall and the glans is in direct contact with the surface against which it is moving. This structural arrangement, wherein the inner diameter of the tubular protective device is larger than a penis, provides greater sensitivity for both partner.

Standards within the industry for condoms, typically, do not define the inner diameter of a condom, but define the acceptable width of the condom when it is laid flat on a surface. A condom having a width of about 47 millimeters to about 51 millimeter is considered, within the industry, to be form fitting. Contoured or loose fitting condoms have a width of about 50 millimeters to about 54 millimeters. For this invention an acceptable width is at least about 50 millimeters in an unstretched state along the entire length of the tube. A desirable range for the width of the tubular protective device of this invention is between about 55 millimeters and about 85 millimeters.

The collar-shaped, outwardly extending portion of the tubular protective device has a means for radially stretching or extending the collar, such as a ring or ring-like member. Furthermore, the ring-like member serves to prevent the open end of the tubular protective device from being pushed into the vagina during sexual intercourse. This "means for extending" the collar or ring-like member, in the most desirable embodiments of the invention, is integrally extruded onto the open end of the tubular protective device and is formed from the same material from which the walls of the device are manaufactured. Such a structure can also be formed by rolling the polymer material, that forms the walls of the device, from the open end of the tube so as to form a ring of material. This ring of material can be maintained by heating the ring or using an adhesive to maintain the structure of the ring and prevent it from unrolling. The ring can also be molded into the open end of the tubular device. The selection between molding or extruding a ring is determined by the material being used to manufacture the device. For example, natural polymers, such as latex are suitable for molding procedures and synthetic thermoplastic polymers, such as many polyurethanes, are suitable for extruding procedures.

The diameter of the means for radially stretching the collar is desirably large enough to prevent the exchange of secretions between partners during sexual intercourse. The diameter of the means for radially stretching the collar is desirably large enough such that the vulva and the base of the penis are covered by the extended collar. The preferred embodiments of the invention have a first diameter for the tube of the device and a second diameter for the means for radially stretching the collar, such as an elastic ring, wherein the second diameter is larger than the first diameter. Acceptable diameters for the means for radially stretching the collar of the device are at least about 50 millimeters and desirably between about 60 and about 75 millimeters. Preferably, the collar is conically shaped and when a tubular protective device having an inner diameter of approximately 50 millimeters is used, the collar, supported by the means for radially stretching, preferably, has an inner diameter of approximately 75 millimeters. Embodiments of the invention have a means for retaining at the closed end of the device and can have straight tubular bodies without a collar. The means for radially stretching the collar or open end of the tubular protective device is commonly called the "outer ring." The invention can be used with embodiments wherein the outer ring is essentially the same diameter as the body of the tubular protective device. The diameter of the tubular protective device in this embodiment can be essentially form fitting for the male, but is preferably a larger diameter as discussed above.

Insertion into the vagina of the tubular protective device of the invention can be done by either the man or the woman. The device can be inserted in the traditional manner wherein the male partner places the device over the penis before coitus. The female partner can insert the device by hand or by means of an insertion probe or applicator.

The tubular protective device is prevented from unintentional removal or from slipping out of the vagina once insertion into the female partner has occurred. Prevention of unintentional removal is accomplished by a means for retaining the device in the vagina or "retaining means." The means for retaining can be fashioned in a variety of structures, but is desirably a circular elastic member such as an elastic ring. This member or ring can be connected to the internal or external wall at or essentially at the closed end of the tubular protective device. After being placed correctly in the vicinity of the uterus, the circular elastic member or elastic ring is maintained within the vagina in the same manner as a diaphragm.

The means for retaining the tubular device in a vagina can comprise one of many structures that are fixed or removable. Ring-like members can provide suitable means for retaining as discussed above. Ring-like members are made more suitable for use as retaining means when at least one segment of the ring is removed. Such embodiments, having a ring with an open segment, permit the ring-like member to be pinched or partially collapsed for easy insertion into the vagina. An open or collapsible retaining means can be desirable in embodiments wherein the means for retaining is other than a ring-like member. Such embodiments can be in the form of ribs that are longitudinally molded into or extruded onto the closed end of the device as well as cap-like retaining means. Regardless of the structure adopted for the retaining means, the retaining means must be structured such that it does not weaken the wall of the tubular protective device nor interfer with coitus, The means for retaining can be made by any method known in the art. A particularly desirable method for providing a retaining means at the closed end of a tubular protective device is extrusion. Extrusion techniques can be used with many polymers. Polyurethanes are especially desirable when used with a method for affixing a retaining means or other "raised structure" to the inner or outer surface of a wall of a tubular protective device. Extrusion procedures can be use before sheets of polymer material are formed into a tubular structure or after the body of the tubular protective device is formed.

The preferred extrusion procedure used with this invention provides a method for affixing a raised structure to a tubular protective device. This method requires providing a preformed tubular protective device, which has an open end and a closed end, on a mandrel. The method then involves extruding at least one projecting bead or raised structure onto the tubular protective device on the mandrel. A least one of the projecting beads, must provide a means for retaining the closed end of the tubular protective device in a vagina of a user. Desirably, the extrusion of the means for retaining is such that it radially extends the closed end. A means for retaining which radially extends the tubular protective device is applied to the outer surface of the wall of the tubular device as the tubular device is held stationary on the mandrel and the mandrel is rotated. A raised polymer bead is extruded from an extruder nozzle as the mandrel rotates the tubular device.

Extrusion procedures must be performed at rates and temperatures of extrusion that enable the extruded raised beads to affix to the wall of the tubular protective device without melting or significantly weakening the wall of the device. The rate and temperature of extrusion is selected according to the polymer materials and equipment being used.

Insertion of the tubular protective device into the vagina can be facilitated by enclosing the closed end of the device in a sheathing which is axially movable relative to the tubular protective device. During the insertion of the tubular protective device into the vagina, the sheathing is moved backwards and, thus, opens for insertion of the closed end of the tubular protective device. Such a sheathing is not typically present if a means for retaining the device in the vagina, such as an elastic ring, is present.

A lubricant is, desirably, applied to the tubular protective device prior to or in connection with the insertion of the tubular protective device. The lubricant is applied at least to the inner side of the device in order to reduce friction during contact with the penis. If desired, a lubricant can also be applied to the exterior side of the device. Application of a lubricant to the exterior side of the tubular protective device can facilitate the insertion of the device into the vagina.

Selection of a desirable lubricant can vary greatly. The selection of a lubricant depends, in part, upon the compatibility of the lubricant with the polymer material used to manufacture the device. Desirable lubricants can include ointments, creams, or water-based mucilages or mucilage-like substances such as cellulose-based lubricants.

The invention is described in more detail with reference to the figures which show desirable embodiments of the tubular protective devices according to the invention.

FIG. 1 is a tubular protective device according to the preferred embodiment of this invention. The tubular protective device 1 has an open end 2. The open end 2 has an outer ring 3. A closed end 4 of the tubular protective device has an inner ring 5. In this embodiment the inner ring 5 radially extends the closed end 4. The inner ring 5 of this embodiment is extruded to the outer surface of the wall of the body 1 of the tubular protective device 1. The embodiment of this figure is made from polyurethane sheets wherein the outer ring 3 and inner ring 5 are extruded to the wall of the tubular protective device 1.

Figure 2:
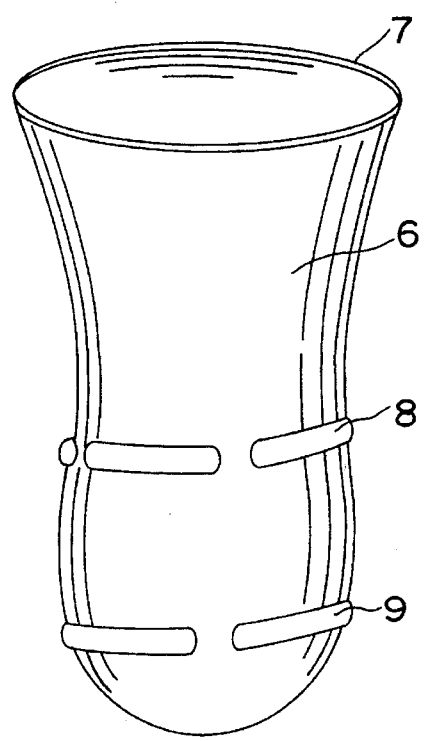
FIG. 2 is a perspective view of an alternative embodiment of the invention having ring-like members for retaining means.

FIG. 2 is an alternative embodiment of a tubular protective device 6 according to this invention. The tubular protective device 6 has an outer ring 7 and two inner-ring like members 8 and 9. Ring-like members 8 an 9 have a plurality of raised or ring segments and open segments. Ring-like member 9 is at the closed end of the tubular protective device 6 and serves as a means for retaining. Inner ring-like member 8 is molded or extruded to the outer surface of the wall of the mid-portion of the tubular protective device 6. Inner ring-like member 8 serves to radially extend a central portion of the tubular protective device 6, but does not effectively retain the closed end of the tubular protective device 6 in the vagina. Both rings-like members 8 and 9 are planar and circular, but are comprised of raised segments such that a unitary ring is not formed. Ring-like members 8 and 9 can be pinched and flattened together to allow an easier insertion of the closed end.

Figure 3:
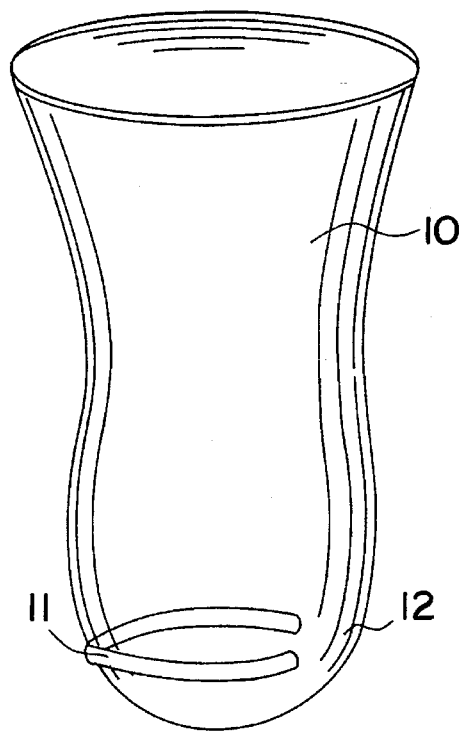
FIG. 3 is a perspective view of an alternative embodiment of the invention having a crescent-shaped retaining means.

FIG. 3 is an alternative embodiment of a tubular protective device 10 according to this invention. A ring-like member 11 is a fixed to the closed end of the tubular protective device 10. The ring-like member 11 has an open segment 12 for collapsing the ring-like member in order to facilitate insertion of the closed end of the tubular protective device.

Figure 4:
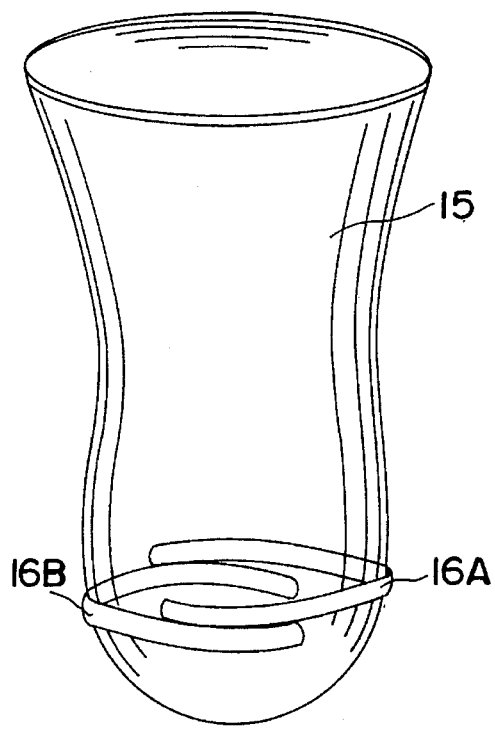
FIG. 4 is a perspective view of an alternative embodiment of the invention having two opposing and partially overlapping crescent-shaped retaining means.

FIG. 4 is an alternative embodiment of a tubular protective device 15 according to this invention. This embodiment has 2 "opposing" crescent-shaped, ring-like members 16A and 16B. Ring-like members 16A and 16B can be compressed, but provide uniform radial extension of the closed end of the tubular protective device 15. The uniform ratial extension is desirable in order to ensure that the closed end is properly seated in the vagina in the same manner that a diaphragm is worn. Additionally, the ring-like members 16A and 16B provide a "ribbed effect" for the tubular protective device 15. It is important to know that the terminal portion of the present ring-like members 16A and 16B are softly roundly so as to prevent uneven stress on the wall of the tubular protective device 15 or interference with coitus.

Figure 5:
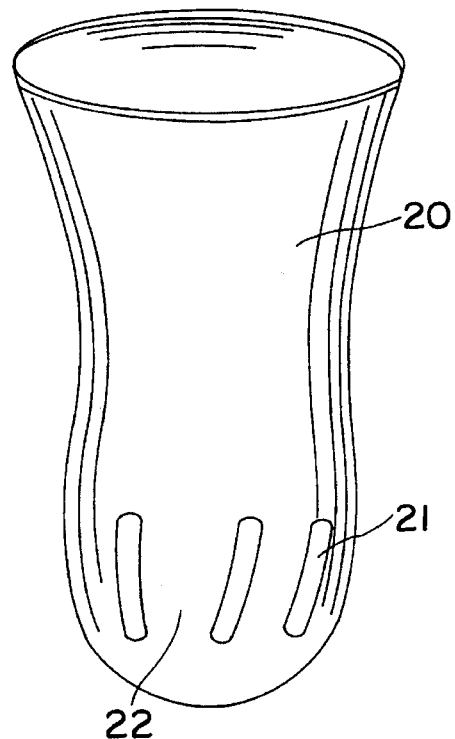
FIG. 5 is a perspective view of the protective device of the preferred embodiment of this invention having longitudinal segments or raised beads for retaining means.

FIG. 5 is an alternative embodiment of a tubular protective device 20 according to this invention. The closed end of this embodiment of the invention has longitudinal segments 21 positioned at the closed end to provide a means for retaining the tubular protective device 20. Desirably, these longitudinal segments 21 are molded or extruded to have a slight curvature along the longitudinal axis of the tubular protective device 20. This curvature enables the longitudinal segments 21 to radially extend the closed end of the tubular protective device 20. The spaces 22 in between the longitudinal segments 21 enable the closed end to be compressed for insertion into a vagina.

Figure 6:
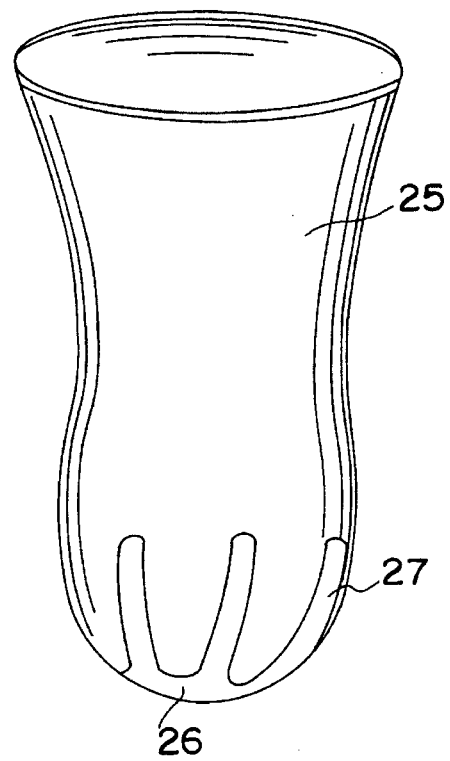
FIG. 6 is a perspective view of an alternative embodiment of the invention having a star-shaped retaining means.

FIG. 6 is an alternative embodiment of a tubular protective device 25 according to this invention. The closed end of this device has a star-shaped retaining means 26. The star-shaped retaining means 26 has a plurality of longitudinal extensions 27 which radially extend the closed end of the tubular protective device 25.

Figure 7:
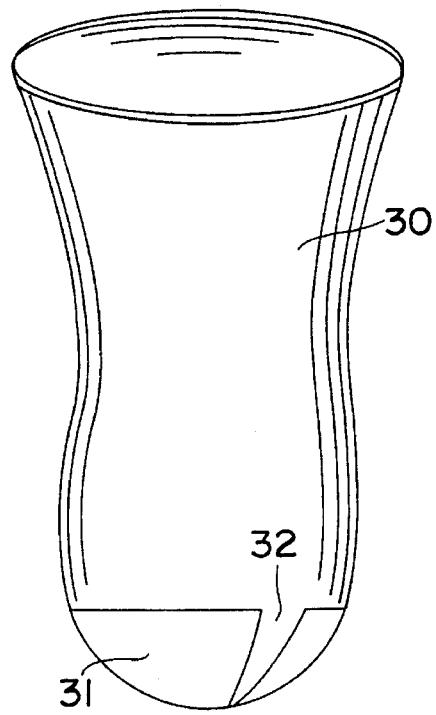
FIG. 7 is a perspective view of an alternative embodiment of the invention having a cap-like retaining means.

FIG. 7 is an alternative embodiment of a tubular protective device 30 according to this invention. This embodiment has a cap-like portion 31 at the closed end of the tubular protective device 25. Cap-like portion 31 has an open segment 32 which can be compressed together for easy insertion of the closed end of the tubular protective device 30. The cap-like portion 31 provides an effective retaining means, but its thickness can interfer with coitus during use of the tubular protective device 30. The cap- like portion 31 can, optionally, have a plurality of open portions 32.

Figure 8:
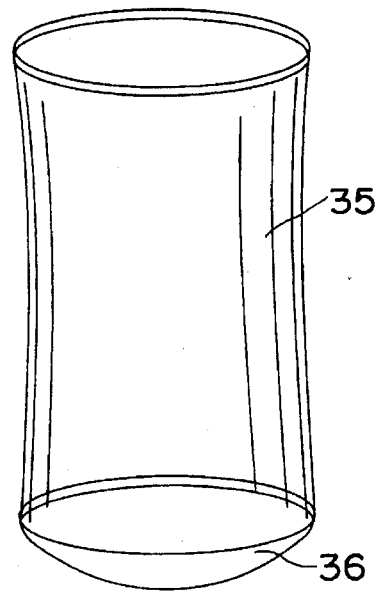
FIG. 8 is a perspective view of an alternative embodiment of the invention having an essentially straight tubular body.

FIG. 8 is an alternative embodiment of a tubular protective device 35 according to this invention. This embodiment has an essentially straight tubular body without a collar portion. This embodiment includes an inner ring 36 at the closed end as a retaining means.

I claim:

1. A tubular protective device for protection against a transfer of infectious matter during sexual intercourse consisting of:

(a) a flexible, thin-walled tube having a continuous thickness between 20 and 60 microns and having a closed end and an open end, said open end having a ring integrally affixed at said open end; and (b) a means for retaining at said closed end of said flexible, thin-walled tube, said means for retaining is at least one crescent-shaped member, said crescent-shaped member radially extends said closed end and maintains said closed end in a vagina of a user.

2. The tubular protective device of claim 1 wherein said means for retaining comprises two opposing crescent-shaped members, each of said crescent-shaped members radially extends said closed end.

* * * * *